United States Patent
Hachiga et al.

(10) Patent No.: US 9,031,640 B2
(45) Date of Patent: May 12, 2015

(54) LASER DOPPLER BLOOD FLOW MEASURING METHOD AND DEVICE

(75) Inventors: Tadashi Hachiga, Imizu (JP); Hiroki Ishida, Imizu (JP); Shunsuke Akiguchi, Imizu (JP); Hiroki Shirakawa, Imizu (JP); Tsugunobu Andoh, Toyama (JP); Yasushi Kuraishi, Toyama (JP)

(73) Assignees: Institute of National Colleges of Technology, Japan, Tokyo (JP); National Univeristy Corporation of Toyama, Toyama (JP)

( * ) Notice: Subject to any disclaimer, the term of this patent is extended or adjusted under 35 U.S.C. 154(b) by 565 days.

(21) Appl. No.: 12/809,738

(22) PCT Filed: Dec. 19, 2008

(86) PCT No.: PCT/JP2008/073245
§ 371 (c)(1),
(2), (4) Date: Jun. 21, 2010

(87) PCT Pub. No.: WO2009/081883
PCT Pub. Date: Jul. 2, 2009

(65) Prior Publication Data
US 2010/0280398 A1 Nov. 4, 2010

(30) Foreign Application Priority Data

Dec. 21, 2007 (JP) .................................. 2007-330112

(51) Int. Cl.
*A61B 5/02* (2006.01)
*A61B 5/0285* (2006.01)
(Continued)

(52) U.S. Cl.
CPC ............. *A61B 5/0285* (2013.01); *A61B 5/0261* (2013.01); *A61B 5/411* (2013.01)

(58) Field of Classification Search
None
See application file for complete search history.

(56) References Cited

U.S. PATENT DOCUMENTS 3,941,477 A * 3/1976 Schodl ............................ 356/28
4,154,529 A * 5/1979 Dyott ............................... 356/28
(Continued)

FOREIGN PATENT DOCUMENTS

JP 05-015501 A 1/1993
JP 07-100119 A 4/1995
(Continued)

OTHER PUBLICATIONS

International Search Report dated Jan. 20, 2009 issued in International Appln. No. PCT/JP2008/073245.
(Continued)

*Primary Examiner* — Nicholas Evoy
(74) *Attorney, Agent, or Firm* — Holtz, Holtz, Goodman & Chick PC

(57) ABSTRACT

[Subject] To provide laser Doppler blood flow measuring method and device which achieve multi-dimensional measurement efficiently at a high degree of accuracy over a wide range with a simple optical system and device.
[Solving Means] Laser light from a semiconductor laser 12 is split and formed into sheet lights Ls using a cylindrical lens 22, and the sheet lights Ls are crossed with each other at a predetermined position. A lens system 30 configured to form an image of scattered lights into a linear shape at a linear irradiation site Lx where the sheet lights Ls cross with each other is provided. An optical fiber array 32 having a plurality of optical fibers 34 is provided at an image-forming position of the lens system 30. Avalanche photodiodes 42 configured to convert the scattered lights which are shifted in frequency by the Doppler effect caused by the blood flow into electric signals for the each optical fiber 34 are provided. The blood flow velocity in a tissue of a biological body at the linear irradiation site Lx is calculated from the scattered lights transformed from the laser light by being shifted in frequency by the Doppler effect and is scanned for the each optical fiber 34, whereby the blood flow velocity in the blood vessel in a predetermined area in the biological body is calculated.

15 Claims, 13 Drawing Sheets

(51) Int. Cl.
*A61B 5/00* (2006.01)
*A61B 5/026* (2006.01)

(56) References Cited

U.S. PATENT DOCUMENTS

| | | | |
|---|---|---|---|
| 4,979,818 A * | 12/1990 | Kobayashi | 356/28 |
| 5,598,841 A * | 2/1997 | Taniji et al. | 600/342 |
| 5,865,828 A * | 2/1999 | Jeng | 606/2 |
| 5,999,836 A * | 12/1999 | Nelson et al. | 600/407 |
| 6,006,128 A * | 12/1999 | Izatt et al. | 600/476 |
| 6,324,420 B1 * | 11/2001 | Kishida et al. | 600/479 |
| 6,332,683 B1 * | 12/2001 | Ono et al. | 351/210 |
| 6,485,413 B1 * | 11/2002 | Boppart et al. | 600/160 |
| 6,535,757 B2 * | 3/2003 | Ono | 600/476 |
| 6,540,981 B2 * | 4/2003 | Klaveness et al. | 424/9.6 |
| 6,549,801 B1 * | 4/2003 | Chen et al. | 600/425 |
| 6,569,104 B2 * | 5/2003 | Ono et al. | 600/504 |
| 6,699,198 B2 * | 3/2004 | Numajiri | 600/504 |
| 6,735,463 B2 * | 5/2004 | Izatt et al. | 600/476 |
| 6,762,827 B2 * | 7/2004 | Aroussi et al. | 356/28 |
| 8,480,579 B2 * | 7/2013 | Serov et al. | 600/363 |
| 8,843,186 B2 * | 9/2014 | Halaka | 600/316 |
| 2002/0008848 A1 * | 1/2002 | Ono | 351/209 |
| 2002/0045834 A1 * | 4/2002 | Numajiri | 600/476 |
| 2003/0133096 A1 * | 7/2003 | Aroussi et al. | 356/28 |
| 2003/0220551 A1 * | 11/2003 | Kimball et al. | 600/345 |
| 2014/0073917 A1 * | 3/2014 | Huang et al. | 600/427 |
| 2014/0160487 A1 * | 6/2014 | Huang et al. | 356/479 |

FOREIGN PATENT DOCUMENTS

| | | |
|---|---|---|
| JP | 08-182658 A | 7/1996 |
| JP | 10-085195 A | 4/1998 |

OTHER PUBLICATIONS

N. Fukuichi et al; A Development of a Two-Component Velocity Profiler Using a Multi-Point LDV and a CCD Area Image Sensor; Society of Instrument and Control Engineers; Mar. 31, 2003; pp. 218-224.

N. Fukuichi et al: A Flow Characteristic at the Reattachment Region of a Two-Dimensional Backward-Facing Step Flow; 2003; No. 02-0690; pp. 25-30.

T. Hachiga et al; Development of a Multi-Point LDV by Using Semiconductor Laser With FFT-Based Multi-Channel Signal Processing; Experiments in Fluids; 1998; pp. 70-76.

N. Fukuichi et al; An Experimental Investigation of a Large-Scale Structure of a Two-Dimensional Backward-Facing Step by Using Advanced Multi-Point LDV; Experiments in Fluids; 2004; pp. 274-281.

N. Fukuichi et al; A Development of a Two-Component Velocity Profiler Using a Fiber Multi-Point LDV and a CCD Area Image Sensor; SICE 2002; pp. 2199-2204.

* cited by examiner

INTERFERENCE FRINGES AT CROSS LINE OF SHEET LIGHTS

PHOTO OF BLOOD VESSEL VIEWED FROM FRONT SURFACE OF EAR

DEPTH FROM SURFACE Z=0.25 mm

RESULT OF THREE-DIMENSIONAL MEASUREMENT OF BLOOD VESSEL

THREE-DIMENSIONAL IMAGING OF BLOOD VESSEL

LASER DOPPLER BLOOD FLOW MEASURING METHOD AND DEVICE

This application is a U.S. National Phase Application under 35 USC 371 of International Application PCT/JP2008/073245 filed Dec. 19, 2008.

TECHNICAL FIELD

The present invention relates to a blood flow measuring method for measuring the state of a blood flow of a biological body using a laser Doppler method, and a blood flow measuring device used for measuring the same.

BACKGROUND ART

Data on blood flow in a human skin relates to various states of the skin such as the state of metabolism activity, the metabolic state, the aging degree, skin cancer, and so on in a skin tissue, and measurement of the blood flow in the skin is important in determining the state of the skin.

The leading cause of death among Japanese is malignant neoplasm, the second leading cause is cardiac disease, and the third leading cause is cerebrovascular disease, and the ratio of death from a vascular lesion is almost the same as that from the malignant neoplasm. In addition, in order to recognize the production and progression of the malignant neoplasm, three-dimensional mapping information about new blood vessels in the periphery and information about the blood flow in the new blood vessels are important. In addition, there is a favorite site of the vascular lesion, and hence temporal and spatial information such as blood flow velocity distribution in the blood vessels is inevitable.

Blood flow measuring methods in recent years include laser Doppler flow velocity measuring method, particle image velocimetry (PIV), micro PIV technique, methods using a ultrasonic blood flowmeter, MRI, CT scan method, and methods on the basis of fusion with numeric simulation. Experiments on biological body include an experiment in the body (In vivo) or an experiment out of the body (In vitro). In general, the PIV measurement which provides information about two-dimensional flow is the in vitro measurement. Since the performances of current MRI and CT scan do not provide sufficient spatial and temporal resolutions, it is difficult to obtain detailed information about the state of a blood circulation using the in vivo measurement.

Accordingly, a measuring method using a laser Doppler system is widely used as a blood flow measuring method because momentary values of blood flow velocities and/or blood flow rate are obtained consecutively in a method non-invasive to the skin. The blood flow measuring method on the basis of the laser Doppler system utilizes monochromaticity and coherency of laser light. If the blood vessel in the skin tissue is irradiated with laser light, the light scattered by blood cells moving in the blood vessel causes a frequency shift by the Doppler effect, whereby the blood flow velocity is obtained on the basis of the amount of the frequency shift.

For example, there is a blood flow measuring device based on the laser Doppler system including a sensor element having a transmitting optical fiber configured to launch laser light onto the skin surface from a light source and a receiving optical fiber configured to receive scattered lights from the skin in pair, both embedded in a probe supporting member which faces the skin. The laser irradiating system on the basis of the laser Doppler method includes a one-beam system which is configured to launch a single beam into a subject and a two-beam system which is configured to split a single beam into two parallel beams, cross the same using a lens or the like, and launch a cross point (point of measurement) into the subject.

In addition, the two-beam measuring method includes a differential method and a reference beam method. The reference beam method splits a single laser beam into two strong and weak beams, and utilizes interference between the light shifted in frequency by the Doppler effect and light scattered by a standstill tissue. As there is a difference in frequency on the order of several hundreds to several tens of Hz between the both scattered lights, the interference between the both lights is detected by a light-receiving element such as a photodiode as electric beat signals, and detected frequency and intensity become signals having values corresponding to the velocity and the number of the blood cells. In addition, the values of these signals are integrated and are converted into signals relating to the flow velocity and the flow rate of the blood flow in the corresponding blood vessel, so that the blood flow rate in the blood vessel is obtained.

In the differential method, a single laser beam is split into two beams, and the two beams are collected and are crossed. At the crossed position, the interference of the scattered lights occurs depending on the directions of irradiation of the laser lights. As the intervals of interference fringes are different depending on the shift amount of the Doppler frequency of the light scattered by the blood cells as particles to be observed, the difference is observed to obtain the blood flow velocity. The differential method has an advantage that the scattered lights can be collected into a wide light-receiving aperture, and hence relatively high signal intensity is obtained.

As disclosed in Patent Document 1, a surface blood flow measuring device provided with a sensor unit having a plurality of sensor elements which detect the surface blood flow of the subject and emit output signals and being brought into abutment with the subject, a signal converting unit configured to converts the output signals from the sensor elements into predetermined measured signals, and a display unit configured to display the measured signals as measured values is also proposed. The surface blood flow measuring device is configured in such a manner that when the sensor unit is brought into abutment with the subject, the output signals are emitted from the respective sensor elements according to the surface blood flow of the subject and are converted into the predetermined measured signals in the output signal converting unit. Since the sensor unit is provided with the plurality of sensor elements, measurement is achieved simultaneously or selectively at a plurality of points in one measurement site. In addition, calibration is also possible by averaging the variations of respective measured values, so that the quantitative measurement is achieved.

As disclosed in Patent Document 2, there is provided a blood flow measuring method on the basis of the laser Doppler system in which light-receiving units are provided at a plurality of positions for at least one light-transmitting unit which launches the laser light onto the subject, the light-receiving units being provided at different distances from the light-transmitting unit, the respective light-receiving units receive scattered lights from the subject, the blood flow rates at the respective light-receiving units are measured, whereby the blood flow rates measured at different depth are recorded simultaneously. In this case, it is preferable to provide a plurality of the light-receiving units at each distance from the light-transmitting unit. It is also preferable to vary the power of the laser light to be launched to the subject. Accordingly, the variations in blood flow rate at each skin tissue can be analyzed, and the blood flow rates in a wide depth range of the skin surface can be recorded at each depth from a shallow portion to a deep portion simultaneously.

Furthermore, as disclosed in Patent Document 3, there is also a blood flow distribution measuring device configured to convert the laser light into sheet light using a cylindrical lens, launch the same via a lens onto a mirror arranged at a focal position of the lens, reflect the same from the mirror in the direction of polarization of the mirror, and measure the blood flow rate two dimensionally.

As disclosed in Non-Patent Documents 1 to 5, laser Doppler current meters which allow multipoint simultaneous measurement using laser sheet light are proposed as a device for measuring the flow velocity of fluid in a conduit or the like other than those in the biometrical bodies are proposed.

Patent Document 1: JP-A-5-15501
Patent Document 2: JP-A-8-182658
Patent Document 3: JP-A-7-100119
Non-Patent Document 1: Collection of Papers from the Society of Instrument and Control Engineers Vol. 39, No. 3 (2003) 218-224
Non-Patent Document 2: Collection of Papers from the Japan Society of Mechanical Engineers (B), Vol. 69, No. 677 (2003-1)25-30
Non-Patent Document 3: Experiments in Fluids 24 (1998) 70-76
Non-Patent Document 4: Experiments in Fluids 36 (2004) 274-281
Non-Patent Document 5: SICE 2002 Aug. 5-7, 2002, Osaka, 2199-2204

DISCLOSURE OF INVENTION

Problems to be Solved by the Invention

A blood flow meter on the basis of the one-beam system in the related art uses a single beam (approx. 1 mm in diameter) as the incident laser light and detects scattered lights using a set of sensors. There are the blood flow meters having a configuration to detect the scattered lights using a plurality of optical fibers or the like, or having a plurality of optical fibers for launching laser light and for detecting light signals, respectively. It can be said that these blood flow meters are based on multipoint measurement using the combination of single point measurements. Therefore, the blood flow rates over a wide range cannot be obtained efficiently and, to be worse, the resolution is low and the portion from which the blood flow rates can be obtained is limited.

In contrast, in the case of the two-beam system, the measuring point is the cross point between the two laser beams, and a smaller measurement volume is sufficient in comparison with the case of the one-beam system, so that a high temporal and spatial resolution (approximately several hundreds of μm) is achieved. A blood flow imaging device measures the blood flow distribution by a scan using a laser beam. The blood flow imaging device having a blood flow meter on the basis of the two-beam system is configured to measure one point using two beams, and obtain the blood flow distribution by scanning using the laser beams. However, although the device on the basis of the two-beam system is capable of performing point measurement at a high temporal and spatial resolution, it is difficult to measure a number of points simultaneously and, if there is a displacement from the blood vessel, a significant error is resulted in measured average blood flow velocity. Therefore, in this case as well, measurement of the blood flow rates in the wide range cannot be achieved.

In the case of the two-beam system, if a plurality of sensor elements are provided by branching the optical fiber, the laser power of each sensor element is lowered, and hence only the blood flow rates of a relatively shallow portion of the skin surface can be measured. In addition, it is difficult to measure the number of points simultaneously, and if there is the displacement from the blood vessel, a significant error is resulted in the measured average blood flow velocity. Even though the measurement depth can be adjusted individually by changing the output power of the laser light, or the distance between the transmitting optical fiber and the receiving optical fiber, that is, the distance between the light-transmitting unit and the light-receiving unit of the sensor element on the surface to come into contact with the skin, the blood flow rates at various measurement depths are not measured simultaneously. Therefore, there is a problem that the blood flow rate distribution in the depth direction cannot be obtained, and hence accurate state analysis of the skin tissue cannot be achieved.

As the blood flow measuring devices disclosed in Patent Documents 1 and 2 also employ the optical fiber and are measuring methods on the basis of the single-point measurement, there is the same problem as described above. Also, the blood flow measuring device disclosed in Patent Document 3 is not a device which has an ability to sense the three-dimensional arrangement of the blood vessels.

The technologies disclosed in Non-Patent Documents 1 to 5 are built on a premise that the positions of the conduit and the direction of flow of the fluid are known in advance, so that they are not the technologies which enable sensing of the position of the blood capillary located at invisible positions.

In view of such conventional background arts, it is an object of the present invention to provide laser Doppler blood flow measuring method and device which achieve multi-dimensional measurement efficiently at a high degree of accuracy over a wide range with simple optical system and device.

Means for Solving the Problems

The present invention is a laser Doppler blood flow measuring method including: splitting laser light emitted from a laser light source, transforming the respective split laser lights into sheet-shaped thin sheet lights, and crossing the same with each other at a predetermined position in a biological body; forming an image of scattered lights into a linear shape at a linear irradiation site where the sheet lights cross with each other; converting the scattered lights which are shifted in frequency by the Doppler effect caused by a blood flow in a blood vessel in the biological body from among the scattered lights incident to a plurality of light-receiving elements arranged linearly at the image-forming position into electric signals for each of photoelectric conversion elements; sensing positional information about the blood vessel in the biological body from the position of the light-receiving element which receives the laser light shifted in frequency by the Doppler effect from among the plurality of light-receiving elements; and calculating the blood flow velocity in the blood vessel on the basis of the Doppler frequency shifts of the laser light caused by the blood flow for each of the photoelectric conversion elements.

In addition, the crossed position of the sheet-shaped laser lights is scanned in the direction crossing the longitudinal direction of the linear scattered light to obtain the blood flow in the blood vessel from the scanned linear scattered light for each of the photoelectric conversion elements and calculate the thickness and the arrangement of the blood vessel in a predetermined area in the biological body.

In addition, the crossed position of the sheet-shaped laser lights is scanned in the direction crossing the longitudinal direction of the linear scattered light to obtain the blood flow velocity in the blood vessel from the scanned linear scattered light for each of the photoelectric conversion elements and calculate the blood flow velocity or the blood flow rate of each of the blood vessels in the predetermined area in the biological body on the basis of the blood flow velocity obtained at the individual linear irradiation sites.

The scan is performed in two directions orthogonal to the longitudinal direction of the linear irradiation site so as to obtain a three-dimensional arrangement of the blood vessel in the predetermined area in the biological body while shifting the linear irradiation site in the direction parallel to the longitudinal direction in sequence and enable display of the arrangement of the blood vessel. A three dimensional blood flow state in the tissue of the biological body is calculated and is made possible to be displayed by the scan.

The present invention also provides a laser Doppler blood flow measuring device including: a laser light source, a beam splitter configured to split laser light emitted from the laser light source; a cylindrical optical system transforming the laser light split by the beam splitter into sheet-shaped thin sheet lights; a light-collecting optical system configured to cross the split sheet lights with each other at a predetermined position in a biological body; an image forming optical system configured to form an image of scattered lights into a linear shape at a linear irradiation site where the sheet lights cross; a plurality of light-receiving elements arranged at an image-forming position of the image forming optical system; photoelectric conversion elements configured to convert the scattered lights incident to the light-receiving elements into electric signals for each of the light-receiving elements; blood flow calculating means configured to calculate the blood flow velocities at the linear irradiation site obtained from the laser lights which are shifted in frequency by the Doppler effect caused by the blood flow in a tissue of the biological body on the basis of the electric signals for each of the photoelectric conversion elements; and laser light scanning means configured to scan a crossed position of the sheet-shaped laser lights in the direction crossing the longitudinal direction of the linear irradiation site, wherein the arrangement of a blood vessel in the biological body in an area scanned by the laser light scanning means is calculated on the basis of the calculation by the blood flow calculating means.

In addition, blood flow rate calculating means configured to calculate the blood flow rate in each blood vessel in the biological body from the blood flow velocity and the arrangement of the blood vessel for each of the photoelectric conversion elements obtained by the blood flow calculating means for the scattered lights at each predetermined position scanned by the laser light scanning means is provided.

The image forming optical system is positioned on the same side as the light-collecting optical system with respect to the tissue of the biological body to be measured, and the light-collecting optical system is positioned between the split sheet lights. The image forming optical system may be arranged on the opposite side of the tissue of the biological body to be measured from the light-collecting optical system.

The light-receiving element is formed of a solid state imaging device having the photoelectric conversion elements arranged integrally on a plane.

Advantage of the Invention

According to the laser Doppler blood flow measuring method and device in the present invention, a direct measurement of the blood flow velocity in the human body at a high order spatial resolution is achieved. In addition, measurement of the blood flow velocity distribution and the temporal variation thereof and measurement of the blood flow velocity in the blood capillary are possible in a relatively thick blood vessel. Then, by the scan using the laser beam, measurements of the effective inner diameter, the blood flow velocity distribution, and the temporal variation thereof of the thick blood vessel, and measurement of the average blood flow velocity in the blood capillary within a predetermined measurement range are possible, and the measurement results as described above may be mapped three-dimensionally within a predetermined measurement range. Also, it does not affect the blood flow by contact and is suitable for measurement of the blood flow in an inflammatory portion, blood capillary of an ear, aorta close to the skin, and vein and the blood flow distribution in these blood vessels, so that measurement results with high reproducibility are obtained.

It is also effective for preventive care, and is extremely effective for measuring the blood flow velocity distribution in a new blood vessel such as skin cancer and the temporal and spatial information thereof, measuring the temporal and spatial information about the blood flow velocity distribution of arteria carotis having a close relation to cerebrovascular diseases and, as another example, for figuring out a mechanism of development of allergic dermatitis as a basic application.

Figure 1:
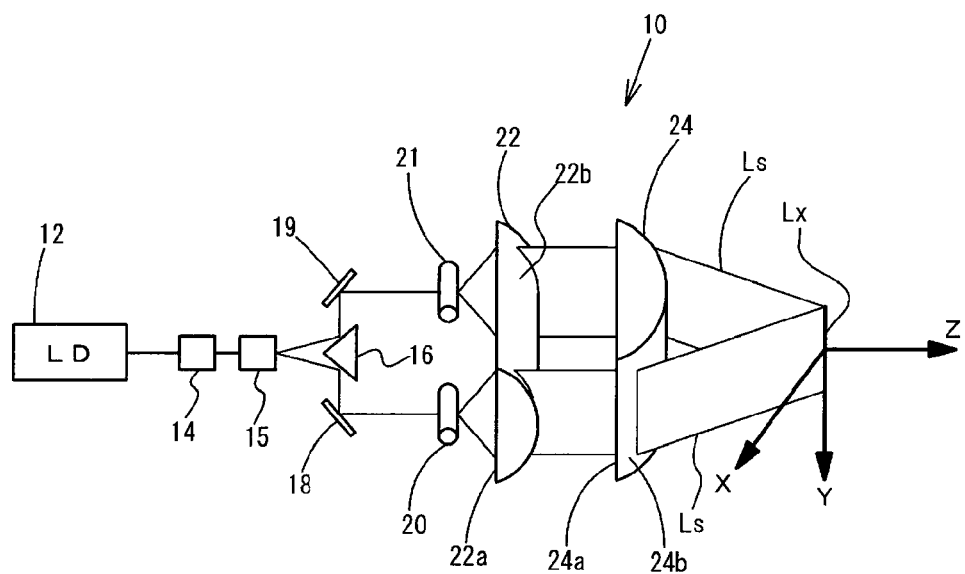
FIG. 1 is a schematic drawing showing an optical system of a light-transmitting unit of a laser Doppler blood flow measuring device according to a first embodiment of the present invention.

REFERENCE NUMERALS 10 laser Doppler blood flow measuring device
12 semiconductor laser
14, 15 acousto-optic device
16 reflecting prism
18, 19 reflecting mirror
20, 21 rod lens
22, 24 cylindrical lens
30 lens system
32 fiber array
34 optical fiber
42 avalanche photodiode
Ls sheet light
Lx linear irradiation site

BEST MODES FOR CARRYING OUT THE INVENTION

Referring now to the drawings, embodiments of the present invention will be described. FIG. 1 to FIG. 9 show a laser Doppler blood flow measuring device according to a first embodiment of the present invention. A laser Doppler blood flow measuring device 10 in this embodiment includes a semiconductor laser 12 such as a laser diode or the like as a laser light source, acousto-optic devices 14, 15 which split continuously oscillating laser light from the semiconductor laser 12 into two beams having slightly different frequencies as shown in FIG. 1. The wavelength of the laser light is preferably a wavelength of approximately 750 to 1500 nm and, for example, near infrared laser having a wavelength of 785 nm is used. This is because the near infrared light has a high transmissivity with respect to a tissue of the biological body.

In addition, there are provided a reflecting prism 16 for reflecting the laser lights split in two directions and reflecting mirrors 18, 19 for reflecting the laser lights reflected by the reflecting prism 16 at a right angle on the light emitting side of the acousto-optic device 15. Furthermore, there are arranged rod lenses 20, 21 provided at a position parallel to each other so that the two laser beams reflected from the reflecting mirrors 18, 19 is launched thereon. The respective rod lenses 20, 21 disperse the incident laser lights and direct the same to a flat surface portion 22a of a first cylindrical lens 22.

The first cylindrical lens 22 is positioned with the flat surface portion 22a faces the rod lenses 20, 21. The two laser lights incident thereto go out from a curved surface portion 22b having the shape of a cylindrical surface of the first cylindrical lens 22, and are formed into two sheet-shaped sheet lights Ls parallel to the center axis of the cylinder of the first cylindrical lens 22 and orthogonal to the flat surface portion 22a. The sheet lights Ls then enters a flat surface portion 24a of a second cylindrical lens 24, which constitutes a light-collecting optical system.

The flat surface portion 24a of the second cylindrical lens 24 faces the same side as the flat surface portion 22a of the first cylindrical lens 22 and is positioned in parallel thereto, and a curved surface portion 24b having the shape of a cylindrical surface, which is the other surface of the second cylindrical lens 24, is arranged in such a manner that the center axis thereof extends orthogonal to that of the first cylindrical lens 22 in a positional relationship of skew lines. The outgoing light from the cylindrical lenses 22, 24 proceed to the same optical path irrespective of which of the flat surface portions 22a, 24a and the curved surface portions 22b, 24b are set as planes of incidence.

In order to restrain the attenuation of the wavelength of the used laser light, the surface of the optical system components used in this embodiment are coated with a reflection preventing film for this wavelength.

The two sheet lights Ls incident to the second cylindrical lens 24 refract and deflect at the curved surface portion 24b so as to cross each other. A crossing of the sheet lights Ls extends linearly as a portion having a high light intensity, and corresponds to a linear irradiation site Lx on the tissue of the biological body.

Figure 2:
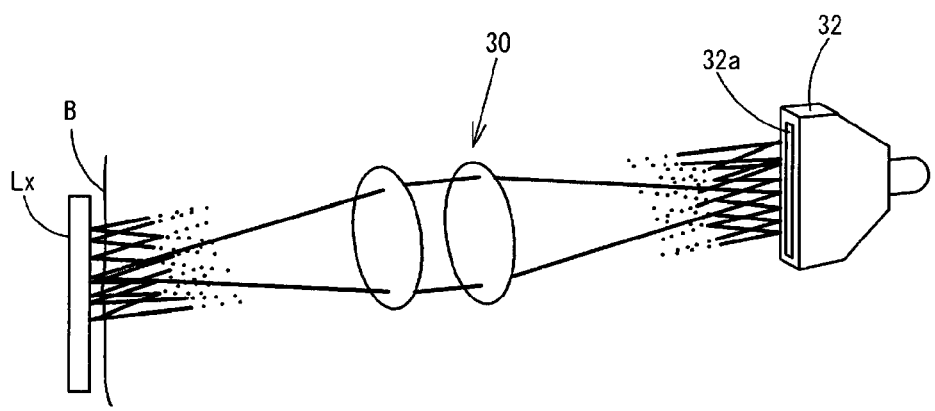
FIG. 2 is a schematic drawing showing an image forming optical system of a light-receiving unit of the laser Doppler blood flow measuring device according to the first embodiment of the present invention.

The scattered lights at the linear irradiation site Lx are converged by a lens system 30 which constitutes an image forming optical system as shown in FIG. 2. The lens system 30 is configured to form an image of the scattered lights at the linear irradiation site Lx on an end surface portion 32a of an optical fiber array 32 as the light-receiving element in a linear shape along the linear irradiation site Lx.

Figure 3:
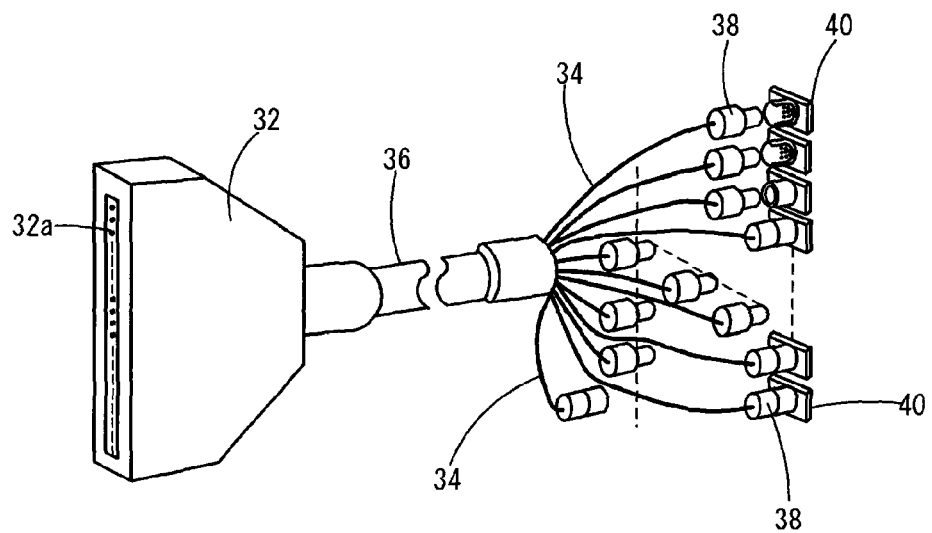
FIG. 3 is a schematic drawing showing an arrangement or the like of a fiber array and optical fibers of the laser Doppler blood flow measuring device according to the first embodiment of the present invention.
Figure 4:
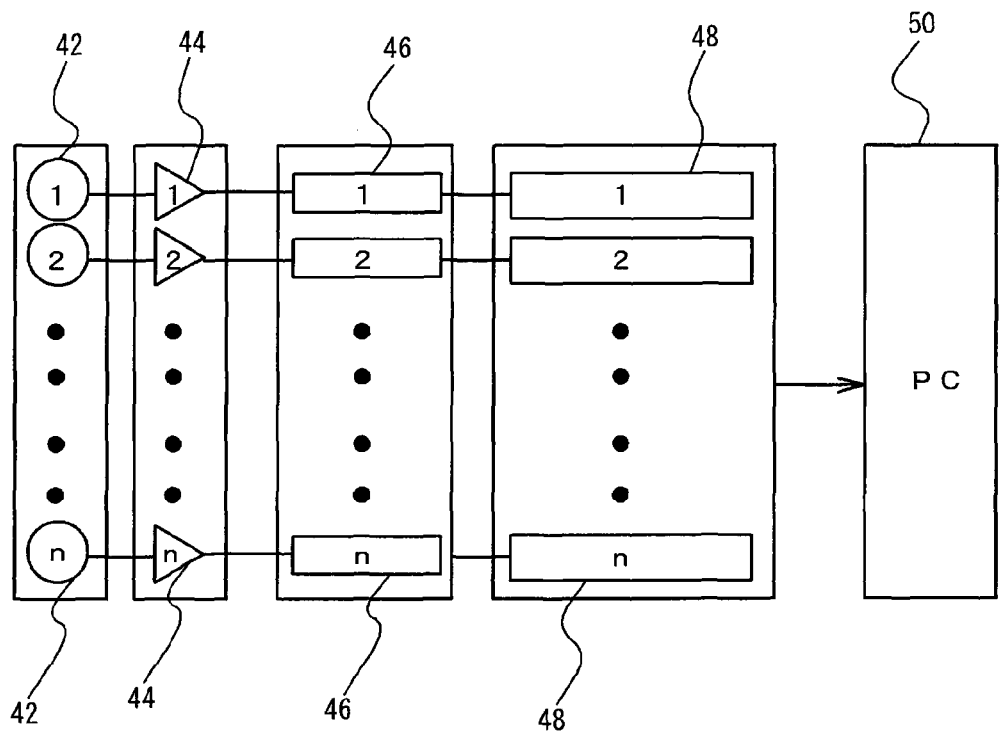
FIG. 4 is a block diagram showing functions from a photoelectric conversion element to a computer of the laser Doppler blood flow measuring device according to the first embodiment of the present invention.

As shown in FIG. 3, the optical fiber array 32 is guided to the other end via optical fibers 34 tied in a light guide bundle 36 and is connected to light plugs 38 in one-to-one correspondence with the optical fibers 34. The light plugs 38 are provided so as to be connectable with a light receptacle 40 individually. The respective light receptacles 40 are provided with avalanche photodiodes 42, which are photoelectric conversion elements, as many as the optical fibers 34 as shown in FIG. 4, and convert respective lights guided by the optical fibers 34 into electric signals, respectively. The outputs from the respective avalanche photodiodes 42 are input to frequency filters 46, respectively, via respective amplifiers 44 provided as many as the optical fibers 34, where signals at predetermined frequency are A/D converted and are recorded in data recorders 48 provided as many as the optical fibers 34. The digital signals recorded in the respective data recorders 48 are input to a computer 50 via a USB connector, and are subjected to a predetermined operation analysis process.

Figure 5:
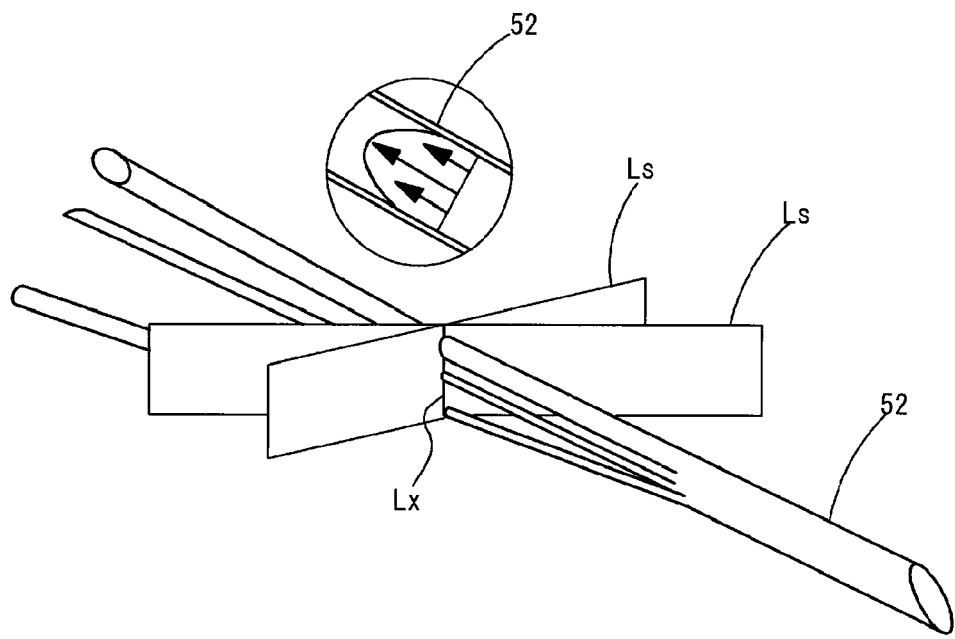
FIG. 5 is a conceptual drawing showing a laser Doppler blood flow measuring method according to the first embodiment of the present invention.
Figure 6:
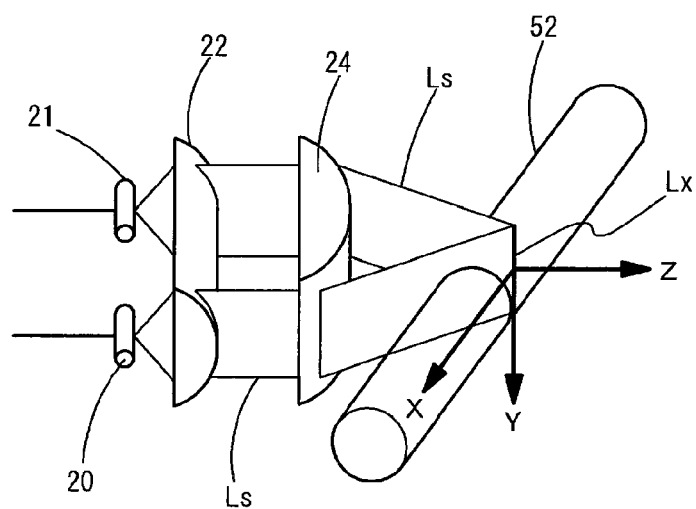
FIG. 6 is a schematic drawing showing an arrangement or the like of the optical system of the laser Doppler blood flow measuring method according to the first embodiment of the present invention.

Subsequently, a laser Doppler blood flow measuring method according to this embodiment will be described. The laser Doppler blood flow measuring method is a method of modulating and splitting laser light emitted from the semiconductor laser 12 by the acousto-optic devices 14, 15, transforming the same into sheet-shaped thin sheet lights Ls using the cylindrical lens 22, crossing the same with each other using the cylindrical lens 24, and forming the linear irradiation site Lx at a predetermined position in a biological body B including a blood vessel 52 as shown in FIG. 5 and FIG. 6. In this state, the blood flow velocity, and the blood flow rate from the blood flow velocity as needed, in the blood vessel 52 can be obtained in the form of a spatial resolution depending on the magnification of the lens system 30, which is the image forming optical system, for each of the optical fibers 34. Here, assuming that the optical fibers 34 having a diameter of 250 μm and the magnification of the optical system is "1", the spatial resolution is 250 μm.

Figure 7:
FIG. 7 is a photo showing interference of laser light in the laser Doppler blood flow measuring method according to the first embodiment of the present invention.

The crossing of the sheet lights Ls extends linearly as a portion having a high light intensity, and corresponds to the linear irradiation site Lx on the tissue of the biological body. The linear irradiation site Lx is formed with interference fringes due to the phase difference of the surfaces of incident waves of the laser lights and the interference fringes as shown in FIG. 7 appear. When the red blood cells pass through this linear area at a certain velocity, the Doppler frequencies of the scattered lights vary. At the linear irradiation site Lx, the Doppler frequencies of the laser lights scattered by the blood cells in the blood flow irradiated with the sheet light Ls vary due to the Doppler effect, which depends on the flow velocity of the blood flow. In the standstill tissue, no variation occurs in Doppler frequencies of the scattered lights. The respective scattered lights at the linear irradiation site Lx are formed into images at respective points corresponding thereto on the optical fiber array 32 by the lens system 30.

Figure 8:
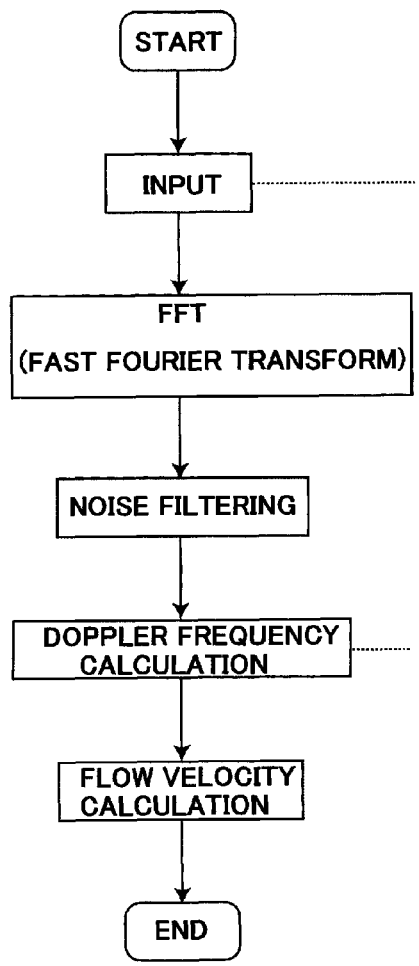
FIG. 8 is a flowchart showing a process in the laser Doppler blood flow measuring method according to the first embodiment of the present invention.
Figure 8:
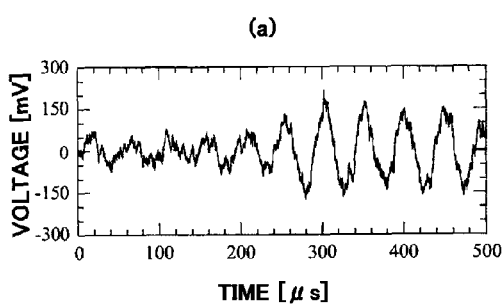
Figure 8:
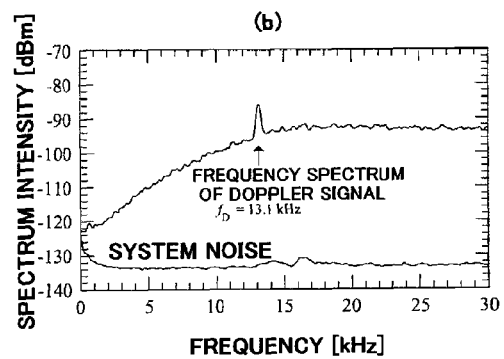

The scattered lights changed in frequency are input to the avalanche photodiode 42 via the optical fibers 34 and redetected as electric beat signals, and the frequency variations and the intensities detected therefrom correspond to the values of the velocities and the numbers of the blood cells. These values are obtained for each of the optical fibers 34, that is, each of the light-receiving units, then the flow velocity of the blood flow at a corresponding portion is calculated, and then the calculated result is integrated on the linear irradiation site Lx, so that the blood flow rate on the corresponding line is obtained. The process to be performed here is shown in FIG. 8. The input signal obtained by the avalanche photodiode 42 is data as shown in a graph (a) in FIG. 8 for example. This data is A/D converted, and is input to the computer, where the digital signal is subjected to fast Fourier transform, then is subjected to noise filtering or the like, whereby the Doppler frequency is calculated. The Doppler frequency is obtained by the appearance of a peak of the Doppler frequency in a frequency spectrum of the detected signal as shown in FIG. 8(b). When the Doppler frequency is obtained, the velocity of the blood cells is calculated from the frequency thereof, and the blood flow velocity is calculated therefrom because the velocity of the blood cells is the flow velocity of the blood flow.

In this embodiment, since the modulation is applied by the acousto-optic device 14, the direction of the blood flow is also discriminated. However, if the discrimination of the direction of flow is not necessary, the measurement is also possible without modulating the frequency by the acousto-optic device 14.

In addition, the linear irradiation site Lx is scanned in the direction orthogonal to the longitudinal direction thereof to obtain the flow rates for the respective optical fibers 34 at a predetermined sampling cycle, whereby the mapping of the blood flow rate in a predetermined plane is formed. Also, by scanning the same in other directions orthogonal to the longitudinal direction of the linear irradiation site Lx, three-dimensional mapping of the blood flow velocity or the blood flow rate is achieved.

Here, when the biological body to be measured is small, a scan of the linear irradiation site Lx is enabled by placing the biological body itself on a table which is movable in the XYZ-axes directions orthogonal to each other and moving the same in these three axes directions. The large biological body such as human can be scanned by driving the optical system such as the cylindrical lenses 22, 24. The crossed position of the sheet lights Ls and the scanning direction thereof at this time can be obtained easily by the calculation for obtaining a point of intersection of lines.

When obtaining the flow velocity in the X-axis direction, the scan is performed by forming the linear irradiation site Lx in the tissue of the biological body B and moving the linear irradiation site Lx relatively in the X-axis direction orthogonal to the longitudinal direction thereof by a predetermined distance as shown in FIG. 9(a). Subsequently, the linear irradiation site Lx is moved further in the Y-axis direction in parallel by the distance corresponding to the length of irradiation, and the scan is repeated in the same manner. Then, as shown in FIG. 9(b), the linear irradiation site Lx is moved by a minute distance in the orthogonal Z-axis direction and the scan is performed in the same manner as described above. This movement and the scan is repeated within the predetermined range. Accordingly, the three-dimensional arrangement of the blood vessel, and the blood flow velocity or the blood flow rate of the corresponding blood vessels within the predetermined range of the biological body B are obtained. Also, when obtaining the flow velocity in the Y-axis direction, the linear irradiation site Lx is arranged in parallel to the X-axis direction, and the scan is performed in the Y-axis direction while shifting in the X-axis direction and then is repeated while moving further in the Z-axis direction as shown in FIG. 9(c).

According to the laser Doppler blood flow measuring method and device in this embodiment, the inner diameter of the blood vessel 52 or the blood flow state in the blood capillary can be measured and mapped three-dimensionally. The spatial resolution in this case may be set to approximately several hundreds of micron. In other words, as the inner diameter of the optical fiber 34 of the optical fiber array which receives the scattered lights at the linear irradiation site Lx along the cross line of the sheet lights Ls corresponds to the spatial resolution, if a diameter of 0.1 mm is chosen for the optical fiber 34, the resolution becomes 0.1 mm, and if a diameter of 0.25 mm is chosen for the optical fiber 34, the resolution becomes 0.25 mm. In addition, the higher resolution is also achieved in proportion to the magnification of the optical system.

By repeating the scan as described above, a solid image of the three-dimensional mapping of the blood flow in the blood capillary is obtained. Accordingly, the blood flow velocity distribution of a given blood vessel (for example, carotid artery) and the temporal variation thereof can be measured. Temporal and spatial information about the blood flow velocity distribution can also be obtained. In addition, the mapping information and the blood flow velocity information about the blood capillary or new blood vessels arranged three-dimensionally can be obtained, so that information about the state of development of cancer or the effect of anticancer drug can also be obtained. Estimation of the effective inner diameter of a thick blood vessel is possible as well.

Figure 10:
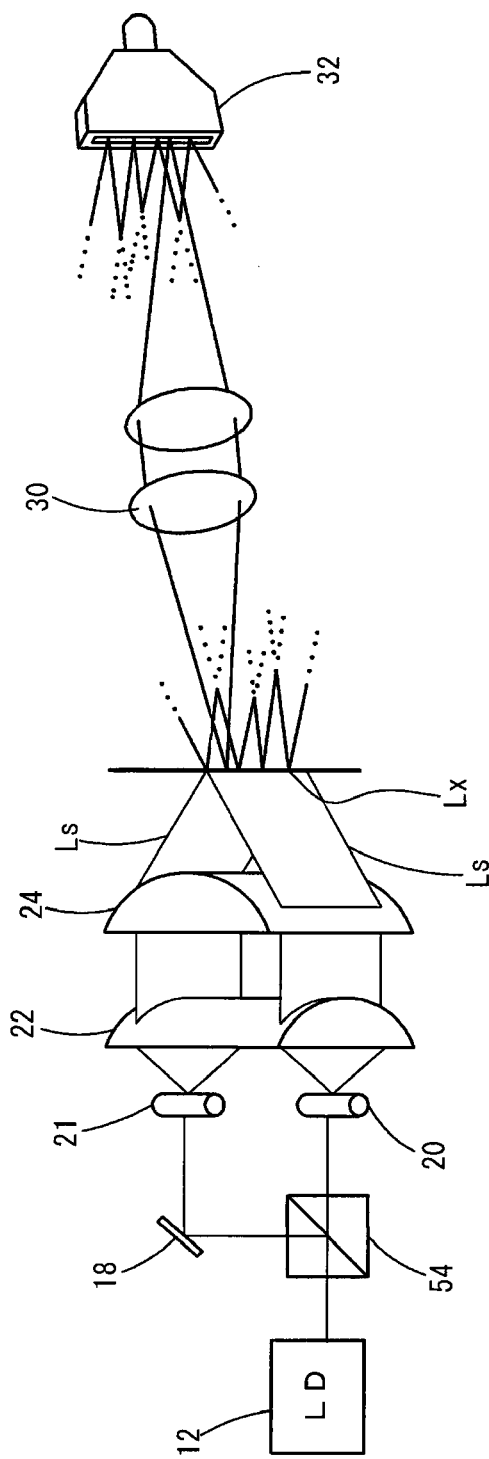
FIG. 10 is a schematic drawing showing an arrangement of the optical system of a laser Doppler blood flow measuring device according to a second embodiment of the present invention.

Subsequently, a second embodiment of laser Doppler blood flow measuring method and device according to the present invention will be described on the basis of FIG. 10. Here, the same configurations as those in the embodiment described above are designated by the same reference numerals and description thereof is omitted. The laser Doppler blood flow measuring device in this embodiment is configured to split the laser light with a beam splitter 54 and form the sheet lights Ls.

The laser Doppler blood flow measuring device in this embodiment is configured to allow the sheet lights Ls to pass through the thin biological body B and direct an image of the scattered lights passed through the linear irradiation site Lx to the optical fiber array 32 via the lens system 30. In this case, the flexibility in arrangement of the optical system is high, and hence the image can be obtained easily.

Figure 11:
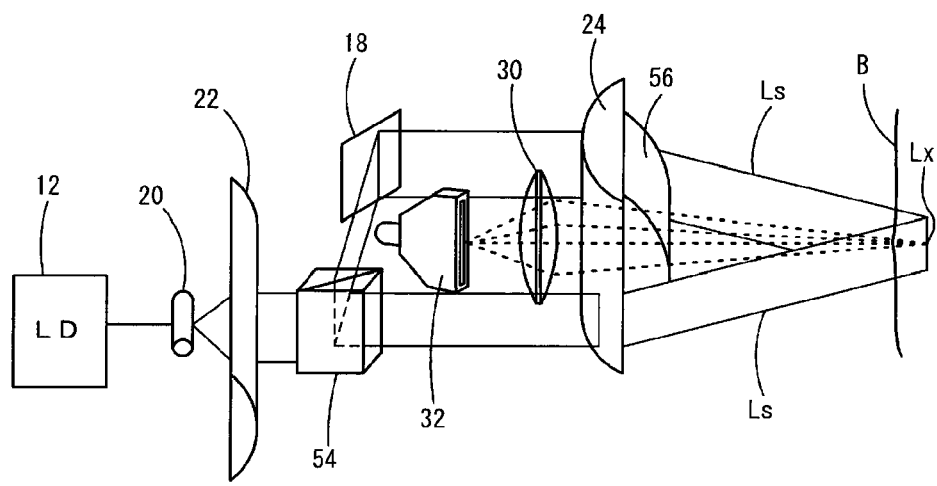
FIG. 11 is a schematic drawing showing an arrangement of the optical system of a laser Doppler blood flow measuring device according to a third embodiment of the present invention.

Subsequently, a third embodiment of laser Doppler blood flow measuring method and device according to the present invention will be described with reference to FIG. 11. Here, the same configurations as those in the embodiment described above are designated by the same reference numerals and description thereof is omitted. The laser Doppler blood flow measuring device in this embodiment is configured in such a manner that the cylindrical lens 22, which forms sheet lights, is arranged on the side of the semiconductor laser 12 with respect to the beam splitter 54. In addition, a cylindrical lens 56 is arranged in an image forming optical system and the optical fiber array 32 is arranged between the sheet lights Ls.

In this case, the scattered lights reflected from the linear irradiation site Lx are introduced into the optical fiber array 32, and the image forming optical system is positioned between the sheet lights Ls, so that the arrangement of the optical system becomes compact and downsizing of the device is achieved.

Figure 12:
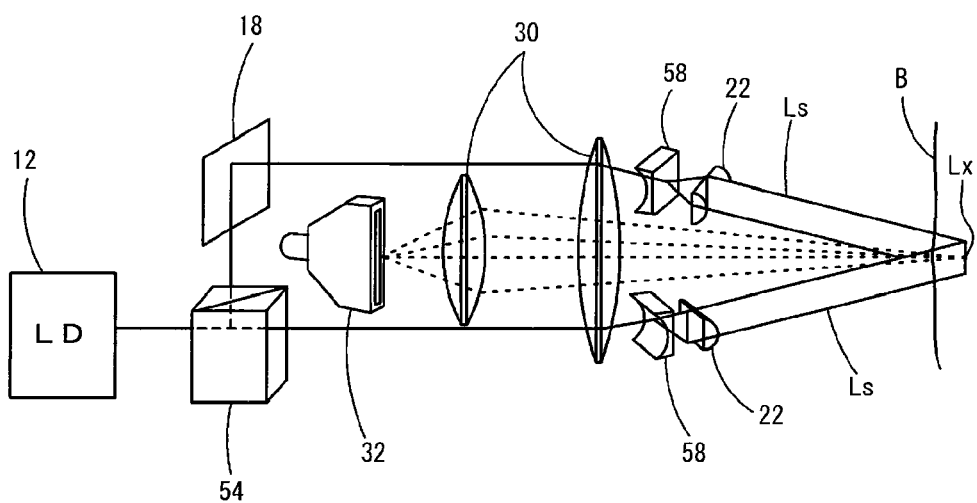
FIG. 12 is a schematic drawing showing an arrangement of the optical system of a laser Doppler blood flow measuring device according to a fourth embodiment of the present invention.

Subsequently, a fourth embodiment of laser Doppler blood flow measuring method and device according to the present invention will be described on the basis of FIG. 12. Here, the same configurations as those in the embodiment described above are designated by the same reference numerals and description thereof is omitted. The laser Doppler blood flow measuring device in this embodiment has the similar optical system to those shown in FIG. 11, and is configured in such a manner that the cylindrical lenses 22, which form sheet lights, are arranged on the side of the biological body B to be measured with respect to the beam splitter 54. In addition, concave lenses 58 which expand the laser lights are arranged upstream of the cylindrical lenses 22, and the number of convex lenses in the lens system 30 of the image forming optical system is increased to suppress aberration.

In addition to the effects which are the same as those of the embodiments described above, this embodiment is effective when the width of the sheet light Ls is several millimeters and the aberration is small.

The laser Doppler blood flow measuring method and device in the present invention are not limited to the embodiments described above. The light-receiving element and the photoelectric conversion element may be a solid state imaging device such as CCD, and a line sensor or an image sensor may be used as the solid state imaging device. The optical fiber may be selected as needed from glass fibers, plastic fiber, and so on.

EXAMPLES

Figure 9:
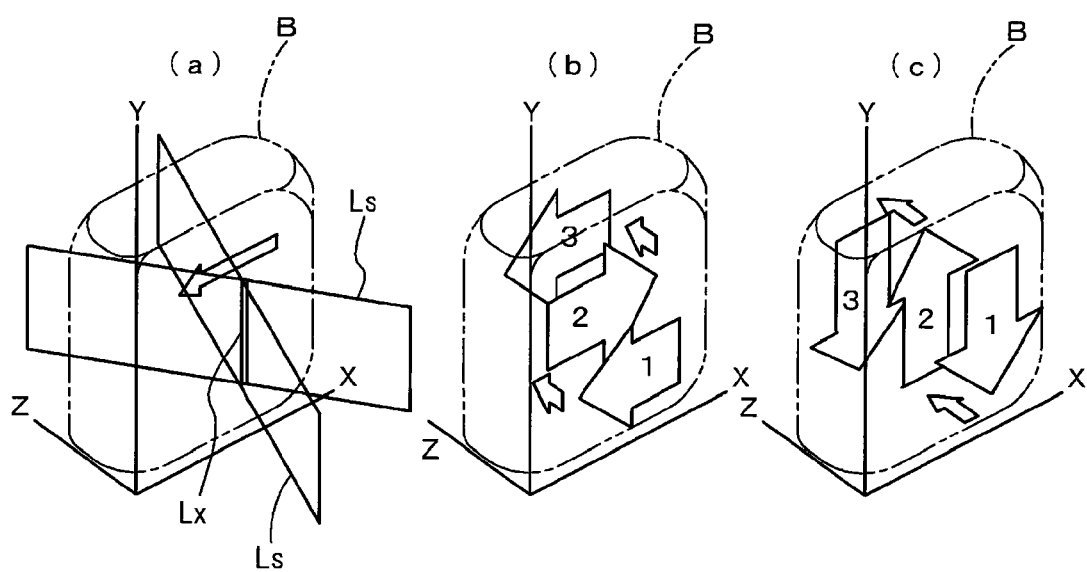
FIG. 9 is a conceptual drawing showing a scanning of a crossing of the laser light in the laser Doppler blood flow measuring method according to the first embodiment of the present invention.
Figure 13:
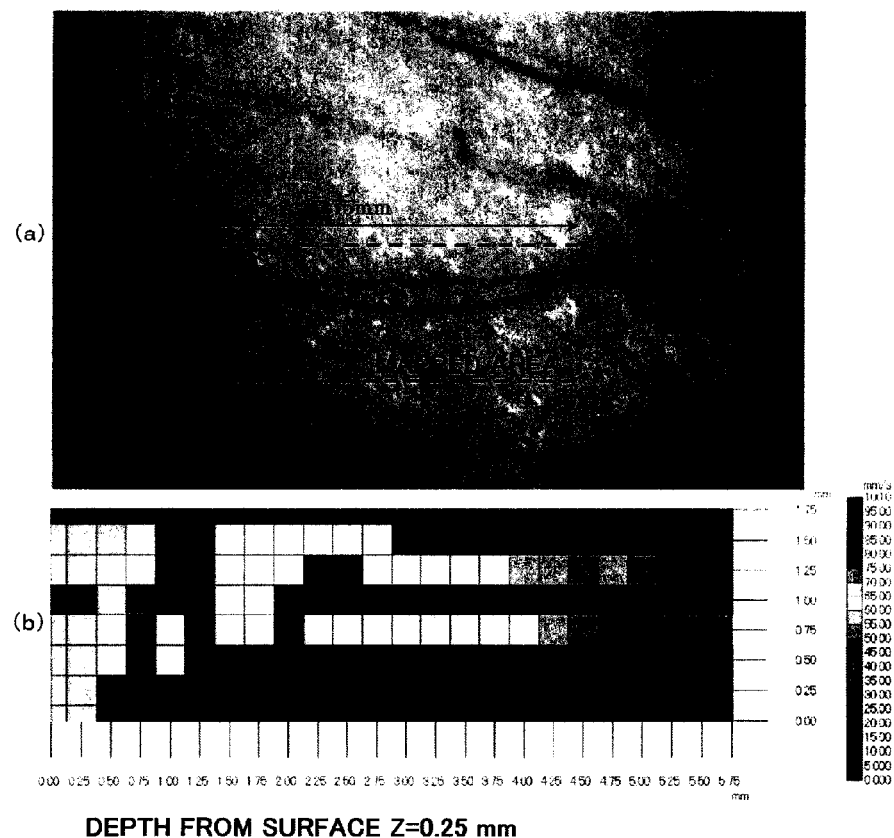
FIG. 13 includes a photo (a) of a portion of an ear of a mouse whose blood flow is measured by the laser Doppler blood flow measuring method in the example of the present invention viewed from the front side, and a drawing (b) of a mapping of the measured results obtained by a scan with the laser beam at a predetermined depth.
Figure 14:
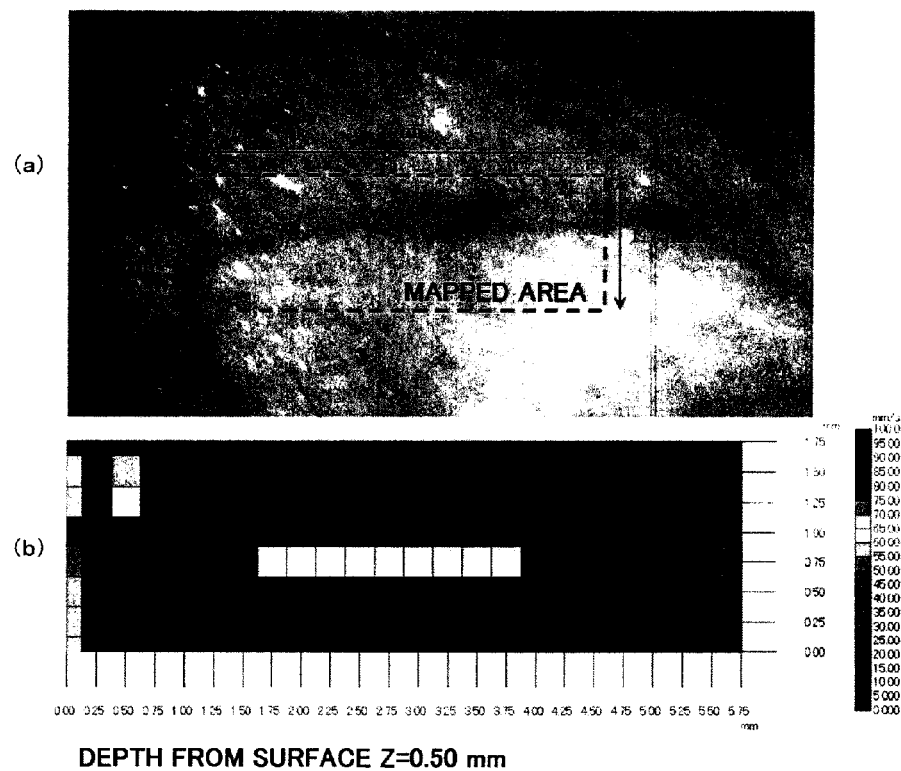
FIG. 14 includes a photo (a) of a portion of an ear of a mouse whose blood flow is measured by the laser Doppler blood flow measuring method in the example of the present invention viewed from the back side, and a drawing (b) of a mapping of the measured results obtained by a scan with the laser beam at a predetermined depth.

Subsequently, an example of a blood flow measurement using the laser Doppler blood flow measuring method and device according to the present invention will be described. In this example, as shown in FIG. 9, a scan was performed with the sheet lights Ls of the laser light, the linear irradiation site Lx of the sheet lights Ls was passed through the thin biological body B, the image thereof was detected, and the blood flow velocity in the tissue of the biological body was calculated and mapped. In the Z-axis direction as the depth direction of the biological body B, scans in the XY-axes directions were performed at different depths of Z=0.25 mm and Z=0.50 mm from the surface side. The mapping results are shown in FIG. 13(*b*) and FIG. 14(*b*). As regards the blood flows in blood vessels appeared in respective photos (a) in FIG. 13 and FIG. 14, the positions of the blood vessels and the blood flow velocities in the respective mapping areas are shown in (b) in the respective drawings.

According to this example, the velocity of the blood flow could be measured by passing the sheet lights Ls through the thin tissue of the biological body, and the arrangement of the blood vessel could also be confirmed.

Figure 15:
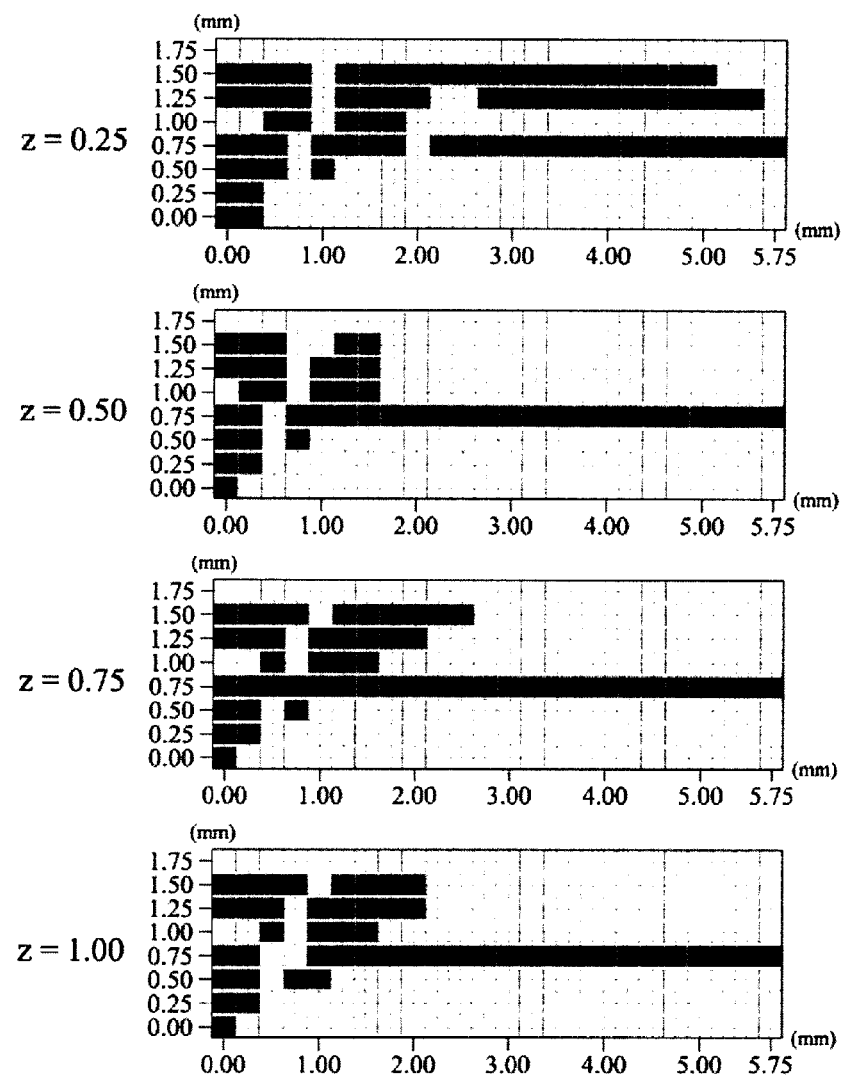
FIG. 15 is a mapping drawing showing the arrangement of blood vessels of the ear of the mouse whose blood flow is measured by the laser Doppler blood flow measuring method in the example of the present invention.
Figure 16:
FIG. 16 is a three-dimensional mapping drawing of the ear of the mouse whose blood flow is measured by the laser Doppler blood flow measuring method in the example of the present invention.
Figure 16:
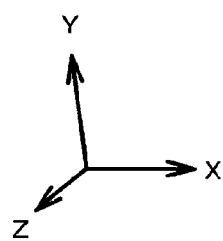

In the example described above, the scan with the sheet lights Ls was further performed in the depth direction, the arrangements of the blood vessel at depths of Z=0.75 mm and Z=1.00 mm were measured, and the results are shown three-dimensionally in FIG. 15 and FIG. 16.

According to the laser Doppler blood flow measuring method and device in the present invention, as shown in FIG. 16, the arrangement of the blood vessel can be viewed three-dimensionally, and hence blood vessel growth in a cancer cell tissue can be grasped with high reliability.

Figure 17:
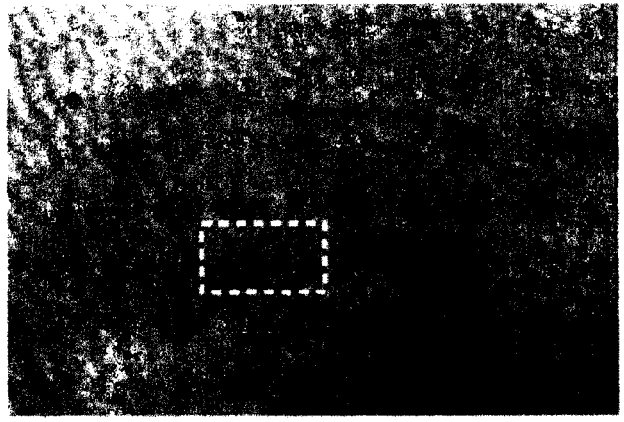
FIG. 17 includes drawings (b) (d) obtained by mapping a photo (a) of the blood flow measured by a reflective device by the laser Doppler blood flow measuring method in the example of the present invention.
Figure 17:
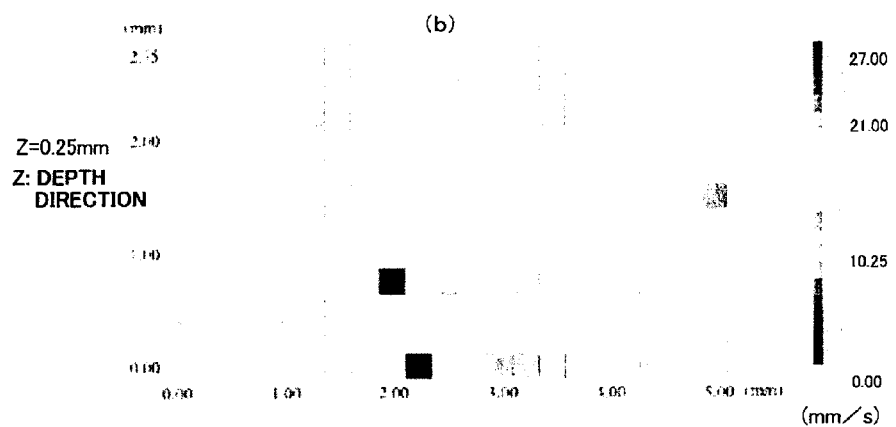
Figure 17:
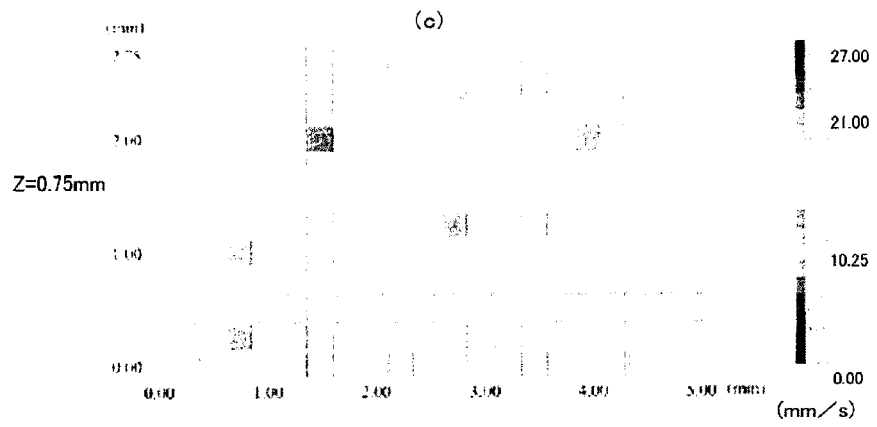

An example shown in FIG. 17 shows an example of measurement with a reflective blood flow measuring device. Scans in the XY-axes directions were performed for an area surrounded by a broken line in a photo shown in FIG. 17(*a*) at different depth of Z=0.25 mm and Z=0.75 mm from the surface side. The positions and the blood flow velocities of the blood vessel in the respective mapping areas are shown in drawings (b) and (c). These drawings show that the three-dimensional arrangement of the blood vessel could be grasped with high degree of reliability also with the device of the reflective type.

The invention claimed is:

1. A laser Doppler blood flow measuring method comprising:
    splitting infrared laser light emitted from a laser light source into split laser lights, transforming the split laser lights into thin sheet lights, and crossing the sheet lights with each other at a linear irradiation site at a position in a biological body, wherein the sheet lights are scattered into scattered lights at the linear irradiation site, and wherein among the scattered lights, scattered lights which are scattered by blood cells in a blood flow in a blood vessel in the biological body are shifted in frequency due to the Doppler effect, and scattered lights which are scattered by stationary tissue are not shifted in frequency due to the Doppler effect;
    receiving, by an optical system, the scattered lights from the linear irradiation site;
    emitting the scattered lights from the optical system such that the scattered lights are in a linear shape and are emitted onto a plurality of light-receiving elements which are arranged in a linear shape;
    performing photoelectric conversion of the scattered lights by a plurality of photoelectric conversion elements which correspond to the plurality of light-receiving elements to obtain electric signals corresponding to the scattered lights;

processing the electric signals obtained by the photoelectric conversion, to obtain frequencies of the scattered lights;

obtaining positional information about the blood vessel in the biological body from positions of ones of the plurality of light-receiving elements which receive the scattered lights which have been shifted in frequency by the Doppler effect; and calculating a blood flow velocity in the blood vessel using Doppler frequency shifts of the scattered lights which were scattered by the blood cells in the blood flow;

wherein the method further comprises scanning the sheet lights to move the linear irradiation site in two directions orthogonal to a longitudinal direction in which the linear irradiation site extends and along a direction parallel to the longitudinal direction, and obtaining information about the blood flow in the blood vessel in three dimensions using the frequencies of the scattered lights at a plurality of positions to which the linear irradiation site is moved by the scanning; and wherein the obtaining of the information about the blood flow in the blood vessel in three dimensions includes obtaining the positional information about the blood vessel and obtaining the blood flow velocity in the blood vessel at the plurality of positions to which the linear irradiation site is moved by the scanning.

2. The method according to claim 1, wherein the optical system is an image forming optical system which is positioned on a same side as a light-collecting optical system which applies the sheet lights to the linear irradiation site.

3. The method according to claim 1, wherein the optical system is an image forming optical system which is positioned on an opposite side of the tissue of the biological body from a light-collecting optical system which applies the sheet lights to the linear irradiation site.

4. The method according to claim 1, wherein the light-receiving elements and photoelectric conversion elements are provided by a solid state imaging device.

5. The laser Doppler blood flow measuring method according to claim 1, wherein a wavelength of the infrared laser light is 750 to 1500 nm.

6. The laser Doppler blood flow measuring method according to claim 2, wherein the plurality of light-receiving elements are positioned between the sheet lights.

7. The laser Doppler blood flow measuring method according to claim 1, wherein the information about the blood flow in the blood vessel in three dimensions includes an inner diameter of the blood vessel.

8. The laser Doppler blood flow measuring method according to claim 1, wherein the information about the blood flow in the blood vessel in three dimensions includes a mapping of the blood flow in the blood vessel in three dimensions.

9. The laser Doppler blood flow measuring method according to claim 1, wherein the information about the blood flow in the blood vessel in three dimensions includes a distribution of the blood flow velocity in three dimensions.

10. The laser Doppler blood flow measuring method according to claim 9, wherein the information about the blood flow in the blood vessel in three dimensions includes information on temporal variation of the distribution of the blood flow velocity in three dimensions.

11. The laser Doppler blood flow measuring method according to claim 1, wherein the information about the blood flow in the blood vessel in three dimensions includes an average blood flow velocity in a measurement range of the blood vessel.

12. The laser Doppler blood flow measuring method according to claim 1, wherein the information about the blood flow in the blood vessel in three dimensions includes a thickness of the blood vessel.

13. The laser Doppler blood flow measuring method according to claim 1, wherein the information about the blood flow in the blood vessel in three dimensions includes a blood flow rate in the blood vessel.

14. The laser Doppler blood flow measuring method according to claim 1, wherein the information about the blood flow in the blood vessel in three dimensions includes an arrangement of the blood vessel in the biological body in three dimensions.

15. The laser Doppler blood flow measuring method according to claim 1, further comprising displaying information about the blood vessel.

* * * * *